United States Patent
Ortyn et al.

(10) Patent No.: US 8,451,524 B2
(45) Date of Patent: May 28, 2013

(54) MODIFYING THE OUTPUT OF A LASER TO ACHIEVE A FLAT TOP IN THE LASER'S GAUSSIAN BEAM INTENSITY PROFILE

(75) Inventors: William Ortyn, Bainbridge Island, WA (US); David Perry, Woodinville, WA (US); Tom Montague, Mercer Island, WA (US)

(73) Assignee: Amnis Corporation, Seattle, WA (US)

( * ) Notice: Subject to any disclaimer, the term of this patent is extended or adjusted under 35 U.S.C. 154(b) by 460 days.

(21) Appl. No.: 12/886,182

(22) Filed: Sep. 20, 2010

(65) Prior Publication Data
US 2011/0085221 A1    Apr. 14, 2011

Related U.S. Application Data

(60) Provisional application No. 61/246,919, filed on Sep. 29, 2009.

(51) Int. Cl.
*G02B 26/08* (2006.01)
*G01N 21/00* (2006.01)

(52) U.S. Cl.
USPC ............... 359/224.1; 359/224.2; 356/338; 356/400

(58) Field of Classification Search
USPC .......... 359/224.1, 224.2, 199.1; 372/29.01, 372/29.014, 31, 32; 356/28, 28.5, 39, 73, 356/301, 317, 326, 338, 400, 419, 445; 250/201.2–201.4
See application file for complete search history.

(56) References Cited

U.S. PATENT DOCUMENTS

| | | | |
|---|---|---|---|
| 3,497,690 A | 2/1970 | Wheeless, Jr. et al. | 250/71 |
| 3,555,280 A | 1/1971 | Richards, Jr. | 250/201 |
| 3,586,760 A | 6/1971 | Dillenburger | 348/339 |
| 3,922,069 A | 11/1975 | Kishikawa et al. | 350/173 |
| 4,313,734 A | 2/1982 | Leuvering | 23/230 |
| 4,414,575 A | 11/1983 | Yamamoto et al. | 348/350 |

(Continued)

FOREIGN PATENT DOCUMENTS

| | | |
|---|---|---|
| EP | 0 154 404 | 9/1985 |
| EP | 0 280 559 | 8/1988 |

(Continued)

OTHER PUBLICATIONS

Lauzon et al., "Flow Cytometric Measurement of Telomere Length," *Cytometry* 42: 159-164, Jun. 2000.

(Continued)

*Primary Examiner* — Frank Font
(74) *Attorney, Agent, or Firm* — Lee & Hayes, PLLC

(57) ABSTRACT

A laser beam is periodically deflected before being directed into a sample volume. The beam is deflected at a frequency such that the beam makes one or more passes through the sample volume while data are collected from the sample volume. The amplitude of motion of the beam, the dwell time of the beam at any given point, and the Gaussian intensity profile of the beam cooperate to produce an effective flat topped illumination profile for the light that is incident on specimens in the sample volume. The total photon exposure at any given point in the sample volume is a function of both the beam intensity and the dwell time at that location. Therefore, a longer dwell time and lower intensity at the edge of the profile are in balance with a shorter dwell time and higher intensity at the center of the profile.

25 Claims, 7 Drawing Sheets

U.S. PATENT DOCUMENTS

| | | | |
|---|---|---|---|
| 4,635,293 A | 1/1987 | Watanabe | 382/44 |
| 4,662,742 A | 5/1987 | Chupp | 356/39 |
| 4,677,680 A | 6/1987 | Harima et al. | 382/1 |
| 4,703,017 A | 10/1987 | Campbell et al. | 436/501 |
| 4,737,932 A | 4/1988 | Baba | 364/900 |
| 4,770,992 A | 9/1988 | Van den Engh et al. | 435/6 |
| 4,777,525 A | 10/1988 | Preston, Jr. | 358/102 |
| 4,786,165 A | 11/1988 | Yamamoto et al. | 356/23 |
| 4,845,197 A | 7/1989 | Petersen et al. | 530/387 |
| 4,857,453 A | 8/1989 | Ullman et al. | 435/7 |
| 5,096,807 A | 3/1992 | Leaback | 435/6 |
| 5,107,522 A | 4/1992 | Kitayama et al. | 375/97 |
| 5,122,453 A | 6/1992 | Martin et al. | 435/7.24 |
| 5,141,609 A | 8/1992 | Sweedler et al. | 204/180.1 |
| 5,153,916 A | 10/1992 | Inagaki et al. | 382/4 |
| 5,159,397 A | 10/1992 | Kosaka et al. | 356/73 |
| 5,159,398 A | 10/1992 | Maekawa et al. | 356/73 |
| 5,159,642 A | 10/1992 | Kosaka | 382/134 |
| 5,247,339 A | 9/1993 | Ogino | 356/73 |
| 5,247,340 A | 9/1993 | Ogino | 356/73 |
| 5,257,182 A | 10/1993 | Luck et al. | 364/413.1 |
| 5,272,354 A | 12/1993 | Kosaka | 250/574 |
| 5,351,311 A | 9/1994 | Rogers et al. | 382/45 |
| 5,372,936 A | 12/1994 | Fraatz et al. | 435/34 |
| 5,422,712 A | 6/1995 | Ogino | 356/73 |
| 5,436,144 A | 7/1995 | Stewart et al. | 435/91.2 |
| 5,444,527 A | 8/1995 | Kosaka | 356/73 |
| 5,459,240 A | 10/1995 | Foxwell et al. | 530/328 |
| 5,471,294 A | 11/1995 | Ogino | 356/73 |
| 5,547,849 A | 8/1996 | Baer et al. | 435/7.24 |
| 5,548,349 A | 8/1996 | Mizuguchi et al. | 348/766 |
| 5,548,395 A | 8/1996 | Kosaka | 356/73 |
| 5,568,315 A | 10/1996 | Shuman | 359/487 |
| 5,596,401 A | 1/1997 | Kusuzawa | 356/23 |
| 5,621,460 A | 4/1997 | Hatlestad et al. | 348/265 |
| 5,625,048 A | 4/1997 | Tsien et al. | 536/23.4 |
| 5,633,503 A | 5/1997 | Kosaka | 250/458.1 |
| 5,644,388 A | 7/1997 | Maekawa et al. | 356/73 |
| 5,674,743 A | 10/1997 | Ulmer | 435/287.2 |
| 5,686,960 A | 11/1997 | Sussman et al. | 348/335 |
| 5,695,934 A | 12/1997 | Brenner | 435/6 |
| 5,733,721 A | 3/1998 | Hemstreet, III et al. | 435/6 |
| 5,754,291 A | 5/1998 | Kain | 356/338 |
| 5,760,899 A | 6/1998 | Eismann | 356/326 |
| 5,764,792 A | 6/1998 | Kennealy | 382/133 |
| 5,784,162 A | 7/1998 | Cabib et al. | 356/456 |
| RE35,868 E | 8/1998 | Kosaka | 250/574 |
| 5,828,776 A | 10/1998 | Lee et al. | 382/133 |
| 5,831,723 A | 11/1998 | Kubota et al. | 356/73 |
| 5,844,670 A | 12/1998 | Morita et al. | 356/124 |
| 5,848,123 A | 12/1998 | Strommer | 378/98.8 |
| 5,855,753 A | 1/1999 | Trau et al. | 204/484 |
| 5,900,942 A | 5/1999 | Spiering | 356/400 |
| 5,926,283 A | 7/1999 | Hopkins | 356/419 |
| 5,929,986 A | 7/1999 | Slater et al. | 356/326 |
| 5,959,953 A | 9/1999 | Alon | 369/44.41 |
| 5,985,549 A | 11/1999 | Singer et al. | 435/6 |
| 5,986,061 A | 11/1999 | Pestka | 530/352 |
| 6,007,994 A | 12/1999 | Ward et al. | 435/6 |
| 6,007,996 A | 12/1999 | McNamara et al. | 435/6 |
| 6,014,468 A | 1/2000 | McCarthy et al. | 382/254 |
| 6,066,459 A | 5/2000 | Garini et al. | 435/6 |
| 6,108,082 A | 8/2000 | Pettipiece et al. | 356/301 |
| 6,115,119 A | 9/2000 | Sieracki et al. | 356/337 |
| 6,116,739 A | 9/2000 | Ishihara et al. | 353/31 |
| 6,156,465 A | 12/2000 | Cao et al. | 430/30 |
| 6,159,686 A | 12/2000 | Kardos et al. | 435/6 |
| 6,210,973 B1 | 4/2001 | Pettit | 436/172 |
| 6,211,955 B1 | 4/2001 | Basiji et al. | 356/326 |
| 6,229,913 B1 | 5/2001 | Nayar et al. | 382/154 |
| 6,249,314 B1 | 6/2001 | Yamamoto et al. | 348/242 |
| 6,249,341 B1 | 6/2001 | Basiji et al. | 356/73 |
| 6,256,096 B1 | 7/2001 | Johnson | 356/335 |
| 6,259,807 B1 | 7/2001 | Ravkin | 381/133 |
| 6,330,081 B1 | 12/2001 | Scholten | 358/463 |
| 6,330,361 B1 | 12/2001 | Mitchell et al. | 382/211 |
| 6,381,363 B1 | 4/2002 | Murching et al. | 382/164 |
| 6,473,176 B2 | 10/2002 | Basiji et al. | 356/326 |
| 6,507,391 B2 | 1/2003 | Riley et al. | 356/28 |
| 6,510,319 B2 | 1/2003 | Baum et al. | 455/442 |
| 6,519,355 B2 | 2/2003 | Nelson | 382/133 |
| 6,522,781 B1 | 2/2003 | Norikane et al. | 382/203 |
| 6,532,061 B2 | 3/2003 | Ortyn et al. | 356/28 |
| 6,548,259 B2 | 4/2003 | Ward et al. | 435/6 |
| 6,549,664 B1 | 4/2003 | Daiber et al. | 382/232 |
| 6,563,583 B2 | 5/2003 | Ortyn et al. | 356/400 |
| 6,580,504 B1 | 6/2003 | Ortyn et al. | 356/338 |
| 6,583,865 B2 | 6/2003 | Basiji et al. | 356/73 |
| 6,608,680 B2 | 8/2003 | Basiji et al. | 356/338 |
| 6,608,682 B2 | 8/2003 | Ortyn et al. | 356/419 |
| 6,618,140 B2 | 9/2003 | Frost et al. | 356/317 |
| 6,620,591 B1 | 9/2003 | Dunlay et al. | 435/7.2 |
| 6,658,143 B2 | 12/2003 | Hansen et al. | 382/133 |
| 6,671,044 B2 | 12/2003 | Ortyn et al. | 356/326 |
| 6,671,624 B1 | 12/2003 | Dunlay et al. | 702/19 |
| 6,707,551 B2 | 3/2004 | Ortyn et al. | 356/338 |
| 6,716,588 B2 | 4/2004 | Sammak et al. | 435/7.23 |
| 6,727,066 B2 | 4/2004 | Kaser | 435/6 |
| 6,763,149 B2 | 7/2004 | Riley et al. | 382/294 |
| 6,778,263 B2 | 8/2004 | Ortyn et al. | 356/28 |
| 6,873,733 B2 | 3/2005 | Dowski, Jr. | 382/232 |
| 6,875,973 B2 | 4/2005 | Ortyn et al. | 250/201.3 |
| 6,906,792 B2 | 6/2005 | Ortyn et al. | 356/28.5 |
| 6,927,922 B2 | 8/2005 | George et al. | 359/708 |
| 6,934,408 B2 | 8/2005 | Frost et al. | 382/129 |
| 6,947,128 B2 | 9/2005 | Basiji et al. | 356/73 |
| 6,947,136 B2 | 9/2005 | Ortyn et al. | 356/338 |
| 6,975,400 B2 | 12/2005 | Ortyn et al. | 356/419 |
| 7,006,710 B2 | 2/2006 | Riley et al. | 382/294 |
| 7,033,819 B2 | 4/2006 | Kim et al. | 435/29 |
| 7,042,639 B1 | 5/2006 | McDowell | 359/398 |
| 7,050,620 B2 | 5/2006 | Heckman | 382/133 |
| 7,057,732 B2 | 6/2006 | Jorgenson et al. | 356/445 |
| 7,079,708 B2 | 7/2006 | Riley et al. | 382/294 |
| 7,087,877 B2 | 8/2006 | Ortyn et al. | 250/201.2 |
| 7,139,415 B2 | 11/2006 | Finkbeiner | 382/128 |
| 7,180,673 B2 | 2/2007 | Dowski, Jr. | 359/637 |
| 7,190,832 B2 | 3/2007 | Frost et al. | 382/173 |
| 7,221,457 B2 | 5/2007 | Jorgenson et al. | 356/445 |
| 7,289,205 B2 | 10/2007 | Yaroslavsky et al. | 356/417 |
| 7,315,357 B2 | 1/2008 | Ortyn et al. | 356/73 |
| 7,450,229 B2 | 11/2008 | Ortyn et al. | 356/326 |
| 7,471,393 B2* | 12/2008 | Trainer | 356/336 |
| 7,522,758 B2 | 4/2009 | Ortyn et al. | 382/133 |
| 7,567,695 B2 | 7/2009 | Frost et al. | 382/129 |
| 7,667,761 B2 | 2/2010 | Thomas | 348/335 |
| 7,729,566 B2* | 6/2010 | Sappey et al. | 385/13 |
| 2001/0006416 A1 | 7/2001 | Johnson | 356/73 |
| 2001/0012620 A1 | 8/2001 | Rich | 435/7.1 |
| 2002/0126275 A1 | 9/2002 | Johnson | 356/317 |
| 2002/0146734 A1 | 10/2002 | Ortyn et al. | 435/6 |
| 2003/0048931 A1 | 3/2003 | Johnson et al. | 382/128 |
| 2003/0049701 A1 | 3/2003 | Muraca | 435/7.23 |
| 2003/0059093 A1 | 3/2003 | Rosania et al. | 382/128 |
| 2003/0104439 A1 | 6/2003 | Finch | 435/6 |
| 2004/0093166 A1 | 5/2004 | Kil | 702/19 |
| 2004/0111220 A1 | 6/2004 | Ochs et al. | 702/19 |
| 2004/0241759 A1 | 12/2004 | Tozer et al. | 435/7.2 |
| 2005/0014129 A1 | 1/2005 | Cliffel et al. | 435/4 |
| 2006/0246481 A1 | 11/2006 | Finch et al. | 435/6 |
| 2006/0257884 A1 | 11/2006 | Brawley et al. | 435/6 |
| 2007/0054350 A1 | 3/2007 | Walker, Jr. | 435/34 |
| 2008/0204719 A1* | 8/2008 | Trainer | 356/73 |
| 2008/0221711 A1* | 9/2008 | Trainer | 700/54 |
| 2008/0240539 A1 | 10/2008 | George et al. | 382/133 |
| 2009/0170149 A1* | 7/2009 | Viator et al. | 435/29 |
| 2009/0202130 A1 | 8/2009 | George et al. | 382/133 |
| 2010/0225913 A1* | 9/2010 | Trainer | 356/338 |
| 2011/0100880 A1* | 5/2011 | Recami et al. | 209/1 |

FOREIGN PATENT DOCUMENTS

| | | |
|---|---|---|
| EP | 0 281 327 | 6/1993 |
| EP | 0 372 707 | 3/1996 |
| EP | 0 950 890 | 10/1999 |
| EP | 1 316 793 | 6/2003 |
| WO | WO 88/08534 | 11/1988 |
| WO | WO 90/10715 | 9/1990 |

| | | |
|---|---|---|
| WO | WO 95/20148 | 7/1995 |
| WO | WO 97/26333 | 7/1997 |
| WO | WO 98/53093 | 11/1998 |
| WO | WO 98/53300 | 11/1998 |
| WO | WO 99/24458 | 5/1999 |
| WO | WO 99/64592 | 12/1999 |
| WO | WO 00/06989 | 2/2000 |
| WO | WO 00/14545 | 3/2000 |
| WO | WO 00/42412 | 7/2000 |
| WO | WO 01/11341 | 2/2001 |
| WO | WO 01/46675 | 6/2001 |
| WO | WO 02/17622 | 2/2002 |
| WO | WO 02/18537 | 3/2002 |
| WO | WO 02/31182 | 4/2002 |
| WO | WO 02/35474 | 5/2002 |
| WO | WO 02/073200 | 9/2002 |
| WO | WO 02/079391 | 10/2002 |
| WO | WO 2005/090945 | 9/2005 |
| WO | WO 2005/098430 | 10/2005 |

OTHER PUBLICATIONS

Levron et al., "Sperm chromosome abnormalities in men with severe male factor infertility who are undergoing in vitro fertilization with intracytoplasmic sperm injection," *Fertility and Sterility* vol. 76, No. 3: 479-484, Sep. 2001.

Lowe et al., "Aneuploid epididymal sperm detected in chromosomally normal and Robertsonian translocation-bearing mice using a new three-chromosome FISH method," *Chromosoma* 105: 204-210, 1996.

Majno et al., "Apoptosis, Oncosis, and Necrosis An Overview of Cell Death," *American Journal of Pathology* vol. 146, No. 1: 3-15, Jan. 1, 1995.

Martin et al., "Detection of aneuploidy in human interphase spermatozoa by fluorescence in situ hybridization (FISH)," *Cytogenetics and Cell Genetics* 64: 23-26, 1993.

Nautiyal et al., "17β-Estradiol induces nuclear translocation of CrkL at the window of embryo implantation," *Biochemical and Biophysical Research Communications* 318: 103-112, 2004.

Oberholzer et al., "Methods in quantitative image analysis." *Histochem Cell Biol*, vol. 105: 333-355, 1996.

Ong, Sim Heng, "Development of a System for Imaging and Classifying Biological Cells in a Flow Cytometer," Doctor of Philosophy Thesis, University of Sydney, School of Electrical Engineering, Aug. 1985.

Ong et al., "Development of an Image Flow Cytometer," *Analytical and Quantitative Cytology and Histology*. XIVth International Conference on Medical and Biological Engineering and the VIIth International Conference on Medical Physics, Finland: 375-382, Aug. 1987.

Ong et al., "Optical Design in a Flow System for Imaging Cells," *Sciences in Medicine*, vol. 14, No. 2: 74-80, 1991.

Ong et al., "Analysis of MTF Degradation in the Imaging of Cells in a Flow System," *International Journal of Imaging Systems & Technology* 5: 243-250, 1994.

Ortyn et al., "Extended Depth of Field Imaging for High Speed Cell Analysis" *Cytometry Part A* 71A: 215-231, 2007.

Pala et al., "Flow cytometric measurement of intracellular cytokines," *Journal of Immunological Methods* 243: 107-124, 2000.

Pang et al., "Detection of aneuploidy for chromosomes 4, 6, 7, 8, 9, 10, 11, 12, 13, 17, 18, 21, X and Y by fluorescence in-situ hybridization in spermatozoa from nine patients with oligoasthenoteratozoospermia undergoing intracytoplasmic sperm injection," *Human Reproduction* vol. 14, No. 5: 1266-1273, 1999.

Patterson et al., "Detection of HIV-1 DNA and Messenger RNA in Individual Cells by PCR-Driven in Situ Hybridization and Flow Cytometry," *Science* 260: 976-979, May 14, 1993.

Perreault et al., "The Role of Disulfide Bond Reduction during Mammalian Sperm Nuclear Decondensation in Vivo," *Developmental Biology* 101: 160-167, 1984.

Pinkel et al., "Cytogenetic analysis using quantitative, high sensitivity, fluorescence hybridization," *Proceedings of the National Academy of Sciences: Genetics* 83: 2934-2938, 1986.

Pollice et al., "Sequential Paraformaldehyde and Methanol Fixation for Simultaneous Flow Cytometric Analysis of DNA, Cell Surface Proteins, and Intracellular Proteins," *Cytometry* 13: 432-444, 1992.

Ried et al., "Simultaneous visualization of seven different DNA probes by in situ hybridization using combinatorial fluorescence and digital imaging microscopy," *Proceedings of the National Academy of Sciences: Genetics* 89: 1388-1392, Feb. 1992.

Robbins et al., "Aneuploidy in sperm of Hodgkin's disease patients receiving NOVP chemotherapy," *The American Journal of Human Genetics* vol. 55, No. 3—Supplement: A68 (371), Sep. 1994.

Robbins et al., "Detection of Aneuploid Human Sperm by Fluorescence In Situ Hybridization: Evidence for a Donor Difference in Frequency of Sperm Disomic for Chromosomes I and Y," *The American Journal of Human Genetics*, 52: 799-807, 1993.

Robbins et al., "Three-probe Fluorescence in situ Hybridization to Assess Chromosome X, Y, and 8 Aneuploidy in Sperm of 14 Men from Two Healthy Groups: Evidence for a Paternal Age Effect on Sperm Aneuploidy," *Reproduction, Fertility and Development* 7: 799-809, 1995.

Robbins et al., "Use of Fluorescence In Situ Hybridization (FISH) to Assess Effects of Smoking, Caffeine, and Alcohol on Aneuploidy Load in Sperm of Healthy Men," *Environmental and Molecular Mutagenesis* 30: 175-183, 1997.

Rufer et al., "Telomere length dynamics in human lymphocyte subpopulations measured by flow cytometry," *Nature Biotechnology* 16: 743-747, Aug. 1998.

Salzman et al., "Light Scatter: Detection and Usage," *Current Protocols in Cytometry* Supplement 9: 1.13.1-1.138.8, 1999.

Satoh et al., "Small Aggregates of Platelets Can Be Detected Sensitively by a Flow Cytometer Equipped With an Imaging Device: Mechanisms of Epinephrine-Induced Aggregation and Antiplatelet Effects of Beraprost." *Cytometry* 48: 194-201, 2002.

Schmid et al., "Evaluation of inter-scorer and inter-laboratory reliability of the mouse epididymal sperm aneuploidy (m-ESA) assay," *Mutagenesis* vol. 16, No. 3: 189-195, 2001.

Schmid et al., "Simultaneous Flow Cytometric Analysis of Two Cell Surface Markers, Telomere Length, and DNA Content," *Cytometry* 49: 96-105, 2002.

Schwerin et al., "Quantification of Y Chromosome Bearing Spermatozoa of Cattle Using In Situ Hybridization," *Molecular Reproduction and Development* 30: 39-43, 1991.

Shi et al., "Aneuploidy in human sperm: a review of the frequency and distribution of aneuploidy, effects of donor age and lifestyle factors," *Cytogenetics and Cell Genetics* 90: 219-226, 2000.

Timm et al., "Amplification and Detection of a Y-Chromosome DNA Sequence by Fluorescence In Situ Polymerase Chain Reaction and Flow Cytometry Using Cells in Suspension," *Cytometry (Communications in Clinical Cytometry)* 22: 250-255, 1995.

Timm et al., "Fluorescent In Situ Hybridization En Suspension (FISHES) Using Digoxigenin-qLabeled Probes and Flow Cytometry," *Biotechniques* vol. 12, No. 3: 362-367, 1992.

Trask et al., "Fluorescence in situ hybridization to interphase cell nuclei in suspension allows flow cytometric analysis of chromosome content and microscopic analysis of nuclear organization," *Human Genetics* 78:251-259, 1988.

Tucker et al., "Extended depth of field and aberration control for inexpensive digital microscope systems" *Optics Express* vol. 4, No. 11: 467-474, May 24, 1999.

van Dekken et al., "Flow Cytometric Quantification of Human Chromosome Specific Repetitive DNA Sequences by Single and Bicolor Fluorescent In Situ Hybridization to Lymphocyte Interphase Nuclei," *Cytometry* 11: 153-164, 1990.

van den Berg et al., "Detection of Y Chromosome by In situ Hybridization in Combination with Membrane Antigens by Two-Color Immunofluorescence," *Laboratory Investigation* vol. 64, No. 5: 623-628, 1991.

Wang et al., "A Novel Apoptosis Research Method With Imaging-Combined Flow Cytometer and HITC OR IR-125 Staining," *Cytometry (Clinical Cytometry)* 50: 267-274, 2002.

Weber-Matthieson et al., "Rapid immunophenotypic characterization of chromosomally aberrant cells by the new FICTION method," *Cytogenetics Cell Genetics* 63: 123-125, 1993.

Weber-Matthieson et al., "Simultaneous Fluorescence Immunophenotyping and Interphase Cytogenetics: A Contribution to the Characterization of Tumor Cells," *Journal of Histochemistry and Cytochemistry* vol. 40, No. 2: 171-175, 1992.

Wietzorrek et al., "A New Multiparameter Flow Cytometer: Optical and Electrical Cell Analysis in Combination With Video Microscopy in Flow," *Cytometry* 35: 291-301, 1999.

Wyrobek et al., "Smokers produce more aneuploid sperm than non-smokers," *The American Society of Human Genetics*, 45th Annual Meeting, A131: 737, Oct. 24-28, 1995.

Wyrobek et al., "Detection of Sex Chromosomal Aneuploidies X-X, Y-Y, and X-Y, in Human Sperm Using Two-Chromosome Fluorescence In Situ Hybridization," *American Journal of Medical Genetics* 53: 1-7, 1994.

Wyrobek et al., "Fluorescence In Situ Hybridization to Y Chromosomes in Decondensed Human Sperm Nuclei," *Molecular Reproduction and Development* 27: 200-208, 1990.

Ferraro et al., "Extended focused image in microscopy by digital holography." *Optics Express*, vol. 13, No. 18: 6738-6749, 2005.

Amann et al., "Fluorescent-Oligonucleotide Probing of Whole Cells for Determinative, Phylogenetic, and Environmental Studies in Microbiology," *Journal of Bacteriology* vol. 172, No. 2: 762-770, Feb. 1990.

Arkesteijn et al., "Chromosome Specific DNA Hybridization in Suspension for Flow Cytometric Detection of Chimerism in Bone Marrow Transplantation and Leukemia," *Cytometry* 19: 353-360, Apr. 1995.

Bains et al., "Flow Cytometric Quantitation of Sequence-Specific mRNA in Hemopoietic Cell Suspension by Primer-Induced in Situ (PRINS) Fluorescent Nucleotide Labeling," *Experimental Cell Research* 208: 321-326, Sep. 1993.

Barren III et al., "Method for Identifying Prostate Cells in Semen Using Flow Cytometry," *The Prostate* 36: 181-188, 1998.

Bauman et al., "Flow Cytometric Detection of Ribosomal RNA in Suspended Cells by Fluorescent In Situ Hybridization," *Cytometry* 9: 517-524, 1988.

Baumgartner et al., "Automated Evaluation of Frequencies of Aneuploid Sperm by Laser-Scanning Cytometry (LSC)," *Cytometry* 44: 156-160, 2001.

Ben-Eliezer et al., "All-optical extended depth of field imaging system," *Journal of Optics A: Pure and Applied Optics* 5: S164-S169, 2003.

Biggs et al., "Acceleration of iterative image restoration algorithms" *Applied Optics* vol. 36, No. 8: 1766-1775, Mar. 10, 1997.

Boyle et al., "Isolation and Initial Characterization of a Large Repeat Sequence Element Specific to Mouse Chromosome 8," *Genomics* vol. 12, No. 3: 517-525, 1992.

Callet-Bauchu et al., "Distribution of the cytogenetic abnormality +i(3)(q10) in persistent polyclonal B-cell lymphocytosis: a FICTION study in three cases," *British Journal of Haematology* 99: 531-536, Dec. 1997.

Ding et al., "Characterization and Quantitation of NF-κB Nuclear Translocation Induced by Interleukin-1 and Tumor Necrosis Factor-α," *The Journal of Biological Chemistry* vol. 273, No. 44: 28897-28905, Oct. 30, 1998.

Disteche et al., "Isolation and characterization of two repetitive DNA fragments located near the centromere of the mouse X chromosome," *Cytogenetics and Cell Genetics* 39: 262-268, 1985.

Dragowska et al., "Measurement of DNA repeat sequence by flow cytometry," *Cytometry* Supplement 7: 51, Oct. 1994.

Engvall, Eva. "Enzyme Immunoassay ELISA and EMIT," *Methods in Enzymology* vol. 70, Part A: 419-439, 1980.

Fernandez-Lago et al., "Fluorescent Whole-Cell Hybridization with 16S rRNA-Targeted Oligonucleotide Probes to Identify *Brucella* spp. By Flow Cytometry," *Journal of Clinical Microbiology* vol. 38, No. 7: 2768-2771, Jul. 2000.

George et al., "Extended depth of field using a logarithmic asphere" *Journal of Optics A: Pure and Applied Optics* 5: S157-S163, 2003.

George et al., "Distinguishing Modes of Cell Death Using the ImageStream® Multispectral Imaging Flow Cytometer," *Cytometry Part A* 59A: 237-245, 2004.

George et al., "Quantitative measurement of nuclear translocation events using similarity analysis of multispectral cellular images obtained in flow," *Journal of Immunological Methods* 311: 117-129, 2006.

Gordy et al., "Visualization of Antigen Presentation by Actin-Mediated Targeting of Glycolipid-Enriched Membrane Domains to the Immune Synapse of B cell APCs." *Journal of Immunology* vol. 172, No. 4: 2030-2038, Feb. 15, 2004.

Hecht, Eugene. "Optics 4th ed." Addison-Wesley Longman, Inc., XP-002465391, ISBN: 0-8053-8566-5, 2002.

Hultdin et al., "Telomere analysis by fluorescence in situ hybridization and flow cytometry," *Nucleic Acids Research* vol. 26, No. 16: 3651-3656, Aug. 15, 1998.

Kubota et al., "Flow Cytometer and Imaging Device Used in Combination." *Cytometry* 21: 129-132, 1995.

Kubota, Fumio. "Analysis of red cell and platelet morphology using an imaging-combined flow cytometer." *Clin. Lab. Haem.* 25: 71-76, 2003.

\* cited by examiner

MECHANICAL FORCE CONSIDERATIONS

| $T=J\omega^2$ | Kg m²/s² | | $A=A_0\omega^2 \sin(\omega t)$ |
|---|---|---|---|
| $J=Ig$ | | | $A_0=1.00$ E-06 |
| $I=t/12b*h^3$ | m⁵ | | $\omega^2=3.95$ E+09 |
| $g=kg/m^3$ | | | |
| | | | $A=3.95$ E+03 |
| $\omega=10000$ | Hz | | |
| $\omega=62832$ | rad/s | | $F=mA$ |
| $\omega^2=3.95$ E+09 | rad²/s² | | $m=2.50$ E-02 |
| | | | $F=98.7$ |
| $t=6.00$ E-03 | m | | $F=22.2$ |
| $b=2.4$ E-02 | m | | |
| $h=2.4$ E-02 | m | | |
| $g=1$ | g/mm³ | | |
| $g=1000000$ | Kg/m³ | | |
| | | | |
| $T=6.55$ E+05 | Nm | | |

MODIFYING THE OUTPUT OF A LASER TO ACHIEVE A FLAT TOP IN THE LASER'S GAUSSIAN BEAM INTENSITY PROFILE

RELATED APPLICATIONS

This application is based on a prior copending provisional application, Ser. No. 61/246,919, filed on Sep. 29, 2009, the benefit of the filing date of which is hereby claimed under 35 U.S.C. §119(e).

BACKGROUND

Lasers are an ideal source to illuminate cellular samples for analysis due to their high brightness, monochromaticity and coherence. Although there are different spatial modes for laser light, the most common is the TEM00 mode in which laser light is generated with a Gaussian intensity profile. The Gaussian intensity profile is governed by the equation $I=I_o *e^{-2(r/w)^2}$, where "$I_o$" is the peak intensity point, "w" is the waist radius (the point where the intensity is 13.5% of the peak intensity) and "r" is distance from the peak. Per the equation, the intensity of the beam begins to fall off immediately on either side of the peak. Assuming a beam waist 85 microns in diameter, the intensity drops to 97% of the peak value at a point just 5.0 microns from the center of the beam. At a point 10 microns from center, the intensity drops to 89% of the peak value. Therefore, when illuminating a core stream containing cells in motion, as is done in flow cytometry, a cell disposed just 5 to 10 microns from the center of the core stream will see a significantly lower level of irradiation and therefore, generate less fluorescence. Because the location of cells in the core stream can vary by these amounts in normal operation of a typical flow cytometer, the laser intensity profile across the beam is a source of measurement variation in these instruments.

In flow cytometry, the laser beam diameter is maintained large relative to the cell and core size, in order to minimize cell-to-cell fluorescence intensity measurement variation. The typical beam size is about 85 microns in diameter for a theoretical core stream size of 10 microns. If the core stream is made larger, then the beam must also be made larger to maintain illumination uniformity. It should be noted that making the core larger may lead to a much higher amount of coincident events in a standard flow cytometer. Although coincidence is not an issue in an imaging flow cytometer, an increase in core size may lead to defocus, which may degrade the imagery. Although making the beam approximately ten times larger than the cell decreases measurement variation, it also wastes a considerable amount of light, thereby decreasing the sensitivity of the instrument, unless this decrease is offset with a higher power and concomitantly higher cost laser. It is therefore desirable to use a higher proportion of the laser light to illuminate a core stream in a flow cytometer without incurring an increase in measurement variation, which should decrease instrument cost by enabling the use of a lower-power laser, or alternatively, increase sensitivity if the same power laser is used. It would also be desirable to actively enable tailoring of the beam profile to further increase sensitivity, where higher amounts of variation are acceptable.

There have been many attempts over the past two decades to generate what are commonly called "flat top" laser profiles to reduce intensity variation near the center of the laser beam. One elegant approach uses diffractive optics, which can be designed to generate a wide array of profiles, including a flat top. Although this approach is effective at generating a flat top, it suffers from the drawback of light loss, reducing overall intensity, and therefore, negating much of the benefit relative to simply increasing beam size.

Another approach disclosed in U.S. Pat. No. 4,826,299 uses a double wedge-shaped optic that is disposed in the laser beam path. The laser beam is then significantly expanded before being imaged into the flow cell. The net effect is the generation of a nearly flat top intensity profile. This method does not suffer the intensity loss associated with diffractive optics and therefore generates a higher intensity than the Gaussian intensity profile with a flat top over the region of interest. When properly designed, this technique can generate a flat top which is 1.5 to 2 times more intense than the standard Gaussian intensity profile, over a 10 micron region around the center of the beam. However, this technique also has several drawbacks. First, the method uses highly specialized optics and requires a substantial expansion of the beam prior to imaging into the flow cell, which adds cost and poses additional constraints on the optical and mechanical design of the instrument. While these issues may theoretically be overcome at a lower cost than using a higher powered laser, this technique relies on superimposing one part of the beam with another in order to smooth out the profile. Since laser light has a high degree of coherence, in practice, the overlapping beams can constructively and/or destructively interfere with each other, generating significant perturbations in the profile. Once the beam is aligned, and a uniform profile is established, very small changes in the position of the beam on the final imaging lens may lead to significant perturbations in the intensity profile. Therefore, very small thermal changes or pointing errors can lead to a loss of uniformity and negate the benefits of the method. Accordingly, an alternative approach is needed to produce a laser beam having a flat top Gaussian beam intensity profile that avoids these problems, and thus, to achieve the benefits of using such a laser beam, as noted above.

SUMMARY

This application specifically incorporates herein by reference the disclosures and drawings of the patent application identified above as a related application.

An exemplary approach has been developed that overcomes the issues associated with the prior art in order to generate a stable, uniform profile at very low cost. The profile optimizes the use of the laser's energy to increase the photon dose experienced by objects flowing through a flow cytometry instrument, thereby increasing the sensitivity of the instrument. Further, the apparatus to implement this approach is easy to manufacture and can be simultaneously applied to multiple lasers within a given system. Further still, the present novel approach provides the ability to actively tailor the beam profile to match various applications after it has been installed in the instrument. The beam may also be tailored to provide for a larger flat top region, at the expense of intensity, to reduce instrument variation when compared to a standard Gaussian intensity profile. The present novel approach can be applied to illuminate cells that are either stationary or in motion, whether in flow or on substrates, but is described below primarily in the context of cells in a flow moving along a one dimensional path.

The present exemplary approach employs a laser beam that is reflected from a mirror, which is in turn, supported on a structure enabling precise rotation of the mirror. The structure rotates about an axis substantially parallel to the axis of cell flow, resulting in a beam scanning motion in a plane substantially perpendicular to the axis of cell flow. It should be understood that other alternative mechanisms can be employed to deflect the laser beam so that it scans in the desired manner. In one exemplary embodiment, the mirror is forced to rotate with a sinusoidal velocity profile at a frequency such that the reflected beam makes one or more passes through the cell core stream during the time in which light from a cell is integrated by the instrument. The mid point of traversal of the laser beam is aligned coincident with the center of the core stream. It is important to note that an amplitude of the scan for the laser beam at the point where the laser beam is incident on a particle is less than the diameter (or less than the largest other cross-sectional dimension) of the laser beam. For example, if the beam waist or cross-sectional dimension of the beam is 25 microns at the point where the laser beam is incident on a particle in the flow stream of the particle analyzer, the beam might scan or deflect across the flow stream by only 9 microns at that point.

The amplitude of the scanning motion, the dwell time of the beam at any given point, and the Gaussian intensity profile of the laser beam all are selected to cooperate in forming an effective flat top illumination profile over the period of integration. The total photon exposure of the cell at any given point in the profile is a function of both the beam intensity and the dwell time at that location. At the edges of the motion, the photon dose is increased, because the beam moves more slowly, offsetting the lower photon dose due the Gaussian intensity profile. Therefore, the longer dwell time and lower intensity at the edge of the profile are in balance with the shorter dwell time and higher intensity at the center of the profile. If the moving beam had a uniform intensity profile instead of a Gaussian intensity profile, the effective profile would provide a higher photon dose at the edges where the beam moves slowly.

It will be readily apparent to those skilled in the art that the means for deflecting the beam may include devices other than a mirror, such as other types of reflective devices, an acousto-optical modulator (AOM), an acousto-optical deflector (AOD), diffractive devices, and other devices that can be controlled to deflect light through a very small angle at a frequency of a few thousand Hertz. Likewise, different variants of this novel approach may employ different beam sizes, motion amplitudes at the point where the beam is incident on particles, motion profiles and the like, without departing from the scope and spirit of the invention. In the context of cells in flow, the photon dose normalization is required in only one axis orthogonal to flow because the motion of the cell in the axis of flow results in a uniform integration of illumination across the cell in the axis of flow. However, those skilled in the art will recognize that stationary cells or other objects can be illuminated uniformly in both axes by implementing the present invention in two axes, either with a second rotating mirror system that acts in series with the first, or by scanning a single mirror (or other appropriate deflecting device) relative to two orthogonal axes.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein:

FIG. 1 schematically illustrates a Gaussian laser beam being reflected from a movable reflective surface, where the motion of the surface sweeps the beam transversely through the sample volume during data collection, effectively producing a flat top illumination profile during the sampling period;

FIG. 2A graphically illustrates a conventional Gaussian intensity profile characteristic of an unmodified laser beam, and a flat top Gaussian intensity profile obtained using the technique illustrated in FIG. 1, where the reflective surface vibrates through a small angle so as to deflect the laser beam repetitively with an amplitude of about 9.6 microns (at the point where the light beam is incident on a particle);

FIG. 2B graphically illustrates an intensity profile as seen by a cell when the cell is illuminated using the technique of FIG. 1, and data are integrated over a period of time;

Figures 1, 3:
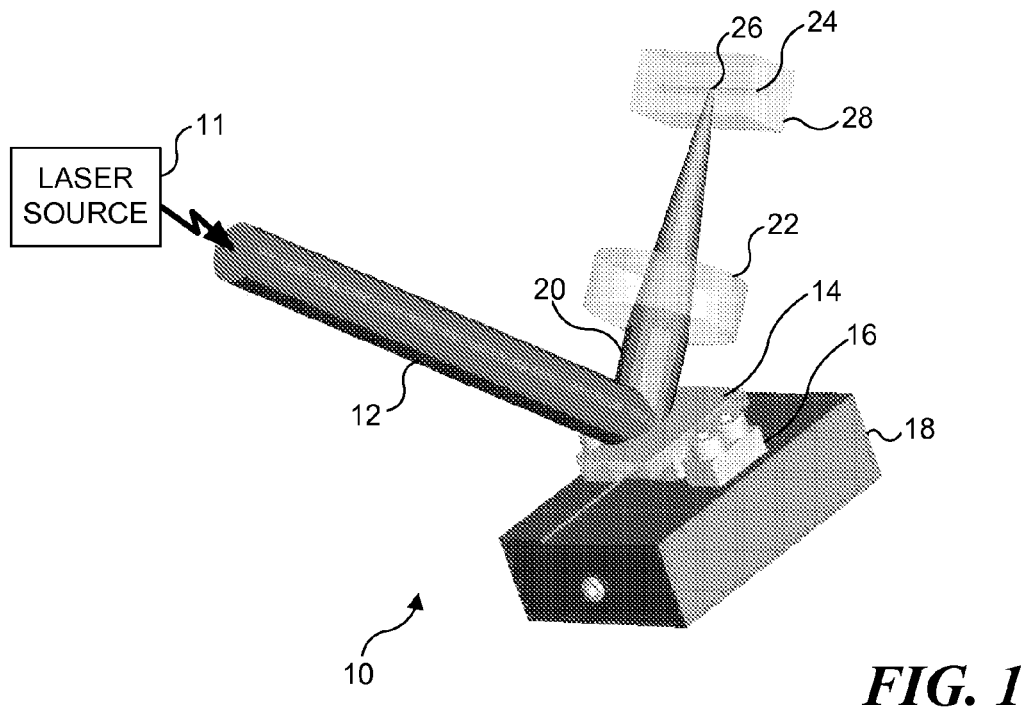
FIG. 3 is a table indicating factors involved in the empirical model used to generate the graphs of FIGS. 2, 4, 5, and 6.
Figure 7:
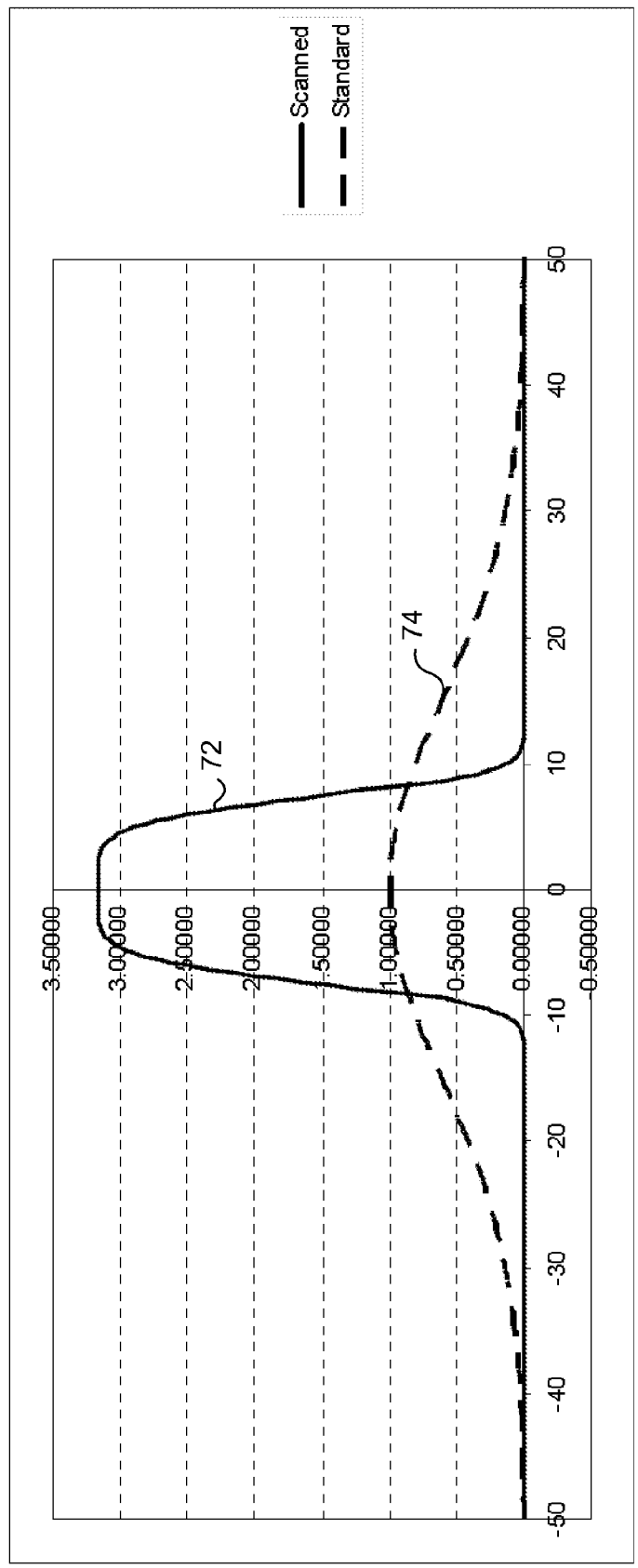
Figure 8A:
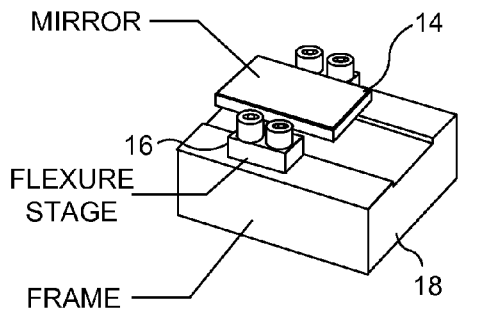
Figure 8C:
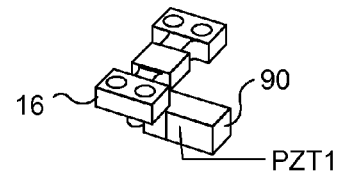
Figure 8B:
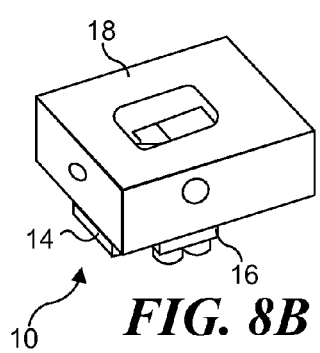
Figure 8D:
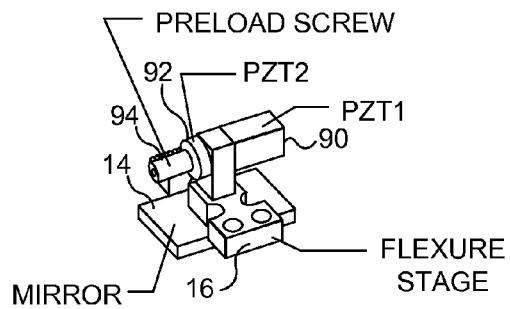
Figure 9:
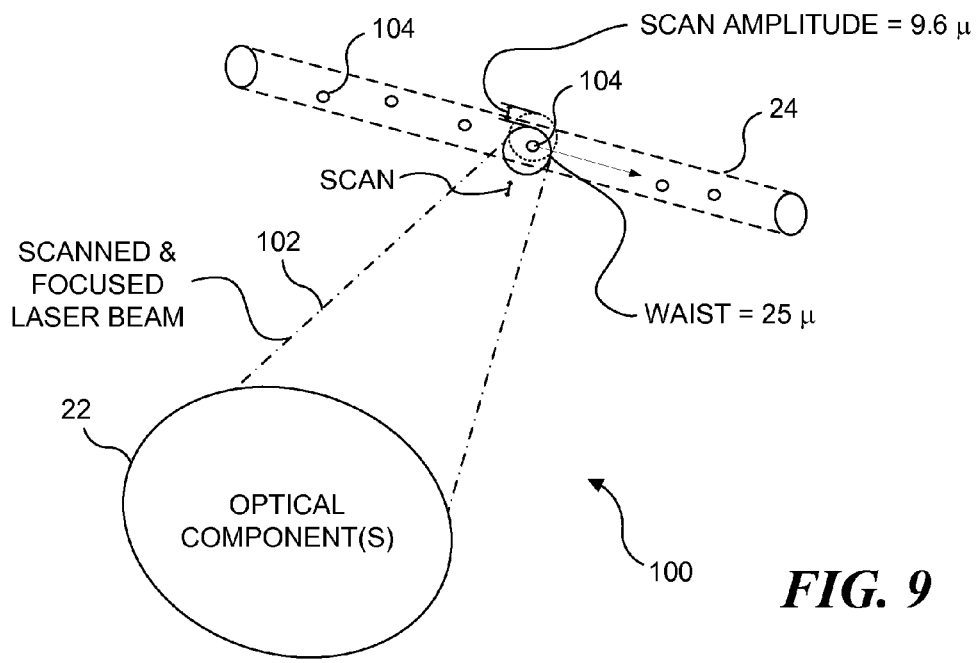

FIG. 7 graphically illustrates a conventional Gaussian intensity profile characteristic of an unmodified laser beam, and a flat top Gaussian intensity profile obtained using the technique illustrated in FIG. 1, where the reflective surface is moved linearly, rather than in a sinusoidal fashion;

FIGS. 8A-8D schematically illustrate different views of an exemplary system including two piezoelectric crystals for moving the reflective surface of FIG. 1, to produce a flat top illumination profile during the sample acquisition, wherein FIG. 8A is an isometric top-side view of the frame, reflective surface and flexure stage, FIG. 8B is an isometric bottom-side view of the same, FIG. 8C is an isometric bottom-side view of the flexure stage and a transducer, and FIG. 8D is an isometric top-side view of a first and second transducer, the reflective surface and the flexure stage; and FIG. 9 is a schematic illustration showing the focused and scanned laser beam incident on a particle in an interrogation region of a particle analyzer.

DESCRIPTION

Figures and Disclosed Embodiments are not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed based on the examples shown in the drawings and discussed herein. Further, it should be understood that any feature of one embodiment disclosed herein can be combined with one or more features of any other exemplary embodiment that is disclosed, unless otherwise indicated.

In FIG. 1, an exemplary embodiment 10 of the present novel approach employs a laser beam 12 with a Gaussian intensity profile, and therefore, no specialized optics are required. In this exemplary embodiment, Gaussian profile beam 12 originating from a laser source 11 has a 1/e² diameter of 700 microns. The laser beam strikes and is reflected from a mirror 14 that is supported on a frame 18 by a flexure stage 16. The reflected laser light is then imaged through at least one optical component 22 (comprising one or more lenses) having a focal length of about 40 mm. The resulting reflected and focused laser beam has a waist of about 25 microns at a point 26 where it is coincident on a core stream 24 passing through a flow cytometer, at a position approximately 54 mm from the lens.

In this exemplary embodiment, mirror 14 is supported on a mount comprising frame 18 with flexure stage 16 allowing a small rotation of the mirror in an axis that is perpendicular to the core stream. In a conventional illumination system for a flow cytometer, the mirror is fixed after alignment and remains motionless during sample acquisition. However, in the present novel approach, flexure stage 16 is driven with a piezoelectric crystal transducer (not shown in this Figure) in order to effect movement of the mirror. Mirror 14 moves so that the reflected laser beam traverses an arc transversely through the flow cell, i.e., in an arc that is at a right angle relative to the direction of travel of a cell or other object carried with flow through the flow cytometer. In one exemplary embodiment, the varying mirror angular position in the optical train and the amount of deflection of the mirror and thus, of the reflected laser beam effected by the piezoelectric crystal transducer cause reflected laser beam 20 to traverse the flow cell in a sinusoidal pattern with about a 9.6 micron amplitude and at a rate that completes at least one cycle during the time the cell traverses the interrogation region of the instrument, where the cell is illuminated by this reflected scanned laser beam. In this and in each of the other exemplary embodiments discussed herein, it must be emphasized that the waist (or diameter, or the largest cross-sectional dimension) of the laser beam at the point where the laser beam traverses the flow cell and may be incident on a particle, is always substantially greater than the extent of scan deflection of the laser beam at that point (e.g., a laser beam with a waist of about 25 microns is scanned with an amplitude at the flow cell of about 9.6 microns in the above example).

The combined effect of the Gaussian beam profile and the sinusoidal motion profile of the reflected laser beam as it traverses the flow cell operate in concert to equalize the photon dose experienced by any object such as a cell at point 28, where the cell is disposed while flowing through an interrogation region. This procedure effectively generates a flat top profile for the laser beam intensity, around the center of core stream 24 in the flow cytometer, as shown for a scanned laser beam solid line curve 32 in a graph 30 of FIG. 2A. Because of the reduced beam diameter caused by one or more optical components 22 focusing the reflected laser beam, the flat top profile has twice the intensity of a conventional 85 micron diameter Gaussian laser beam, as indicated by a dash line curve for the conventional (i.e., non-scanned) laser beam, while maintaining an intensity uniformity equivalent to or better than the 85 micron Gaussian beam within +/−5 μm of the peak intensity. The focusing of the beam thus produces a laser beam with a smaller waist and higher intensity, but the scanning of the laser beam by the mirror effectively flattens the intensity profile of the beam as the reflected and focused laser light fully illuminates a cell or other particle in the interrogation region of the flow cytometer with the scanned light.

Figure 2A:
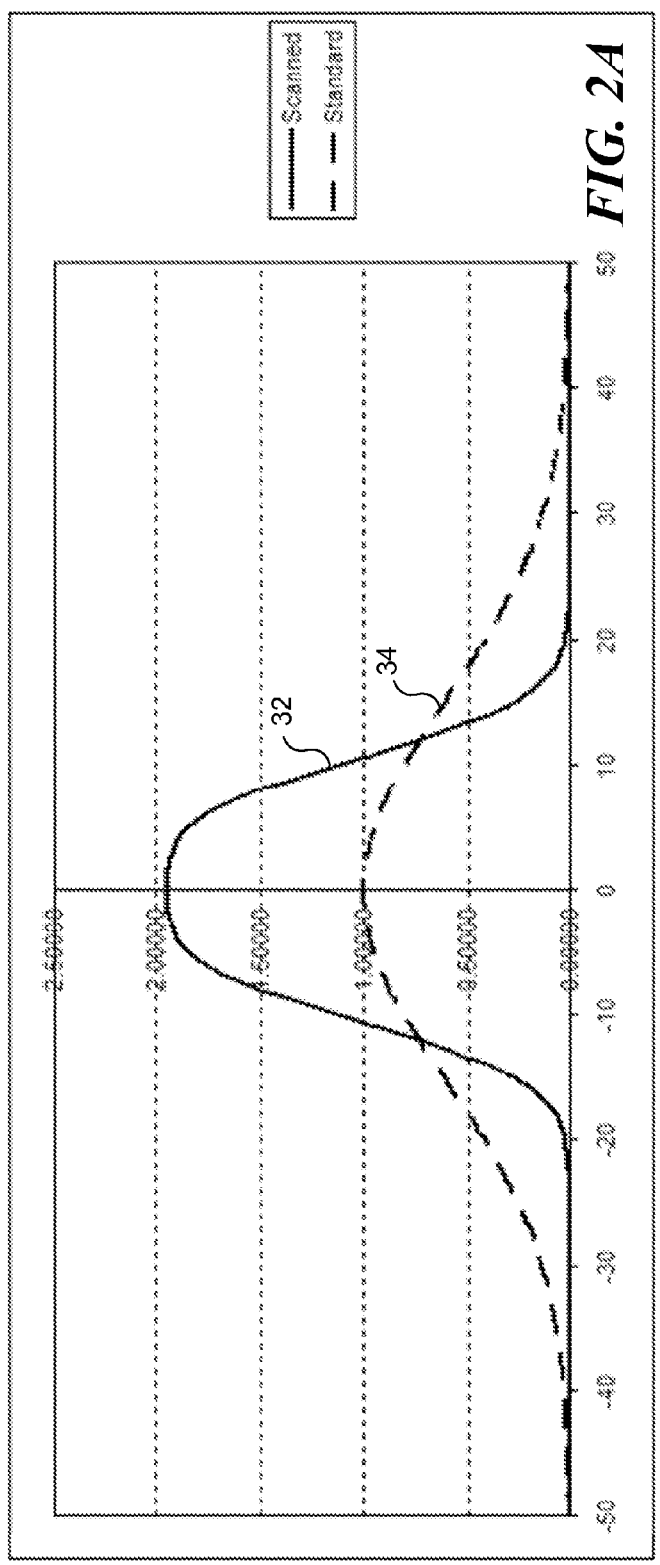

The intensity profiles of both the scanned flat top (solid line 32) and conventional Gaussian (dash line 34) intensity profile laser beams are shown in FIG. 2A. Data (i.e., light rays) are collected from the sample volume using, for example, a time delay integration detector, so that the data are integrated over the sample time. Since data are integrated during the entire traversal of the sample passing through the interrogation region before being read off the time delay integration detector, it appears to the cell as if a single non-scanned beam with a flat topped intensity profile (as shown by flat peak 38 in graph 36 of FIG. 2B) were being imaged into the sample volume of the flow cytometer.

Note that in the example of FIG. 2A, the laser beam reflected from the moving reflective surface of mirror 14 and focused by one or more optical components 22 has a beam waist of only about 25 microns, yet provides the same range and 195% of the intensity obtained using a conventional laser beam having a larger 85 micron beam waist. Because the diameter of the laser beam waist is related to power, the smaller 25 micron scanned laser beam is a more efficient illumination source than the 85 micron conventional laser beam.

FIG. 2A thus compares the Gaussian beam intensity profiles of a standard laser beam having an 85 micron beam waist with that of a smaller 25 micron beam waist laser scanned rapidly with mirror in the horizontal axis to achieve ~10 scan cycles while data are being collected (i.e., where the sample volume is a flow cell and the sample is a biological cell, data are collected during the time required for the biological cell to pass through a field of view in the sample volume (i.e., a flow cell/sample cuvette)). The beam waist as the term is used herein refers to the cross-sectional dimension of the beam at the point where the beam is incident on a sample, e.g., the biological cell, in a particle analyzer. Scanning the laser beam with the mirror effectively generates a broader, flat topped Gaussian beam intensity profile. Since the laser beam used in the scan has a smaller waist, its peak intensity is higher than the Gaussian peak of the standard (non-scanned) laser beam and therefore, the scanned laser beam generates more fluorescence output from the cell or other target specimen on which it is incident. Computational analysis can be used to compute the effective profile for various waist sizes, different amounts of scan amplitude, and different scan profiles (sinusoidal, linear, binary, etc.) to determine how the range and intensity of the scanned beam compares to a fixed beam of a given size (i.e., a given beam waist). Thus, the 85 micron conventional beam and the 25 micron scanned beam discussed above are simply exemplary and are not in any way intended to be limiting on the present novel approach.

Because the relationships between beam waist, scanning parameters and intensity are predictable, computational analysis enables the effect of changing variables such as beam waist and scanning parameters to be determined using a computer model. Such an empirical computer model was developed using a conventional spreadsheet application. The empirical model was developed using the following concepts. With a fixed beam, the photon dose at a given point in the flow cell is strictly a function of the beam's intensity profile. When the beam is scanned through the sample volume, the photon dose at any location in the flow cell is the product of the intensity of the beam at that location (which changes as it scans), multiplied by the dwell time of the beam at that location. If the beam has a Gaussian intensity profile and the scan function is sinusoidal, the effective beam intensity profile is the product of those two functions, with the specific shape of the curve being dependent on the width of the Gaussian profile and the amplitude of the sinusoid. FIG. 3 is a table indicating factors involved in the empirical model used to generate graph 30 in FIG. 2A, a graph 36 in FIG. 2B, graphs 40 and 46 in FIG. 4, graphs 50 and 56 in FIG. 5, and graphs 60 and 66 in FIG. 6.

Figure 2B:
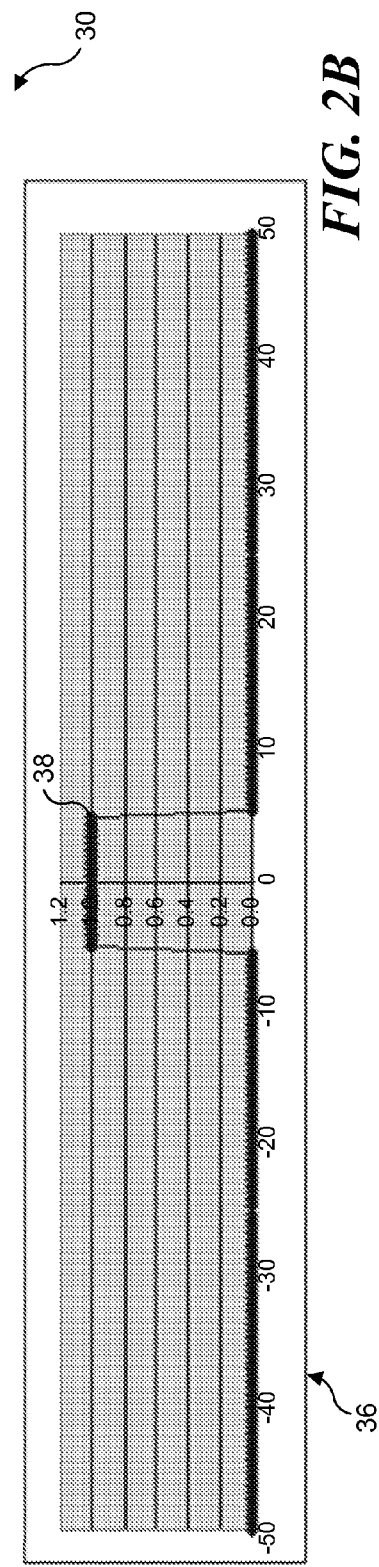
Figure 4:
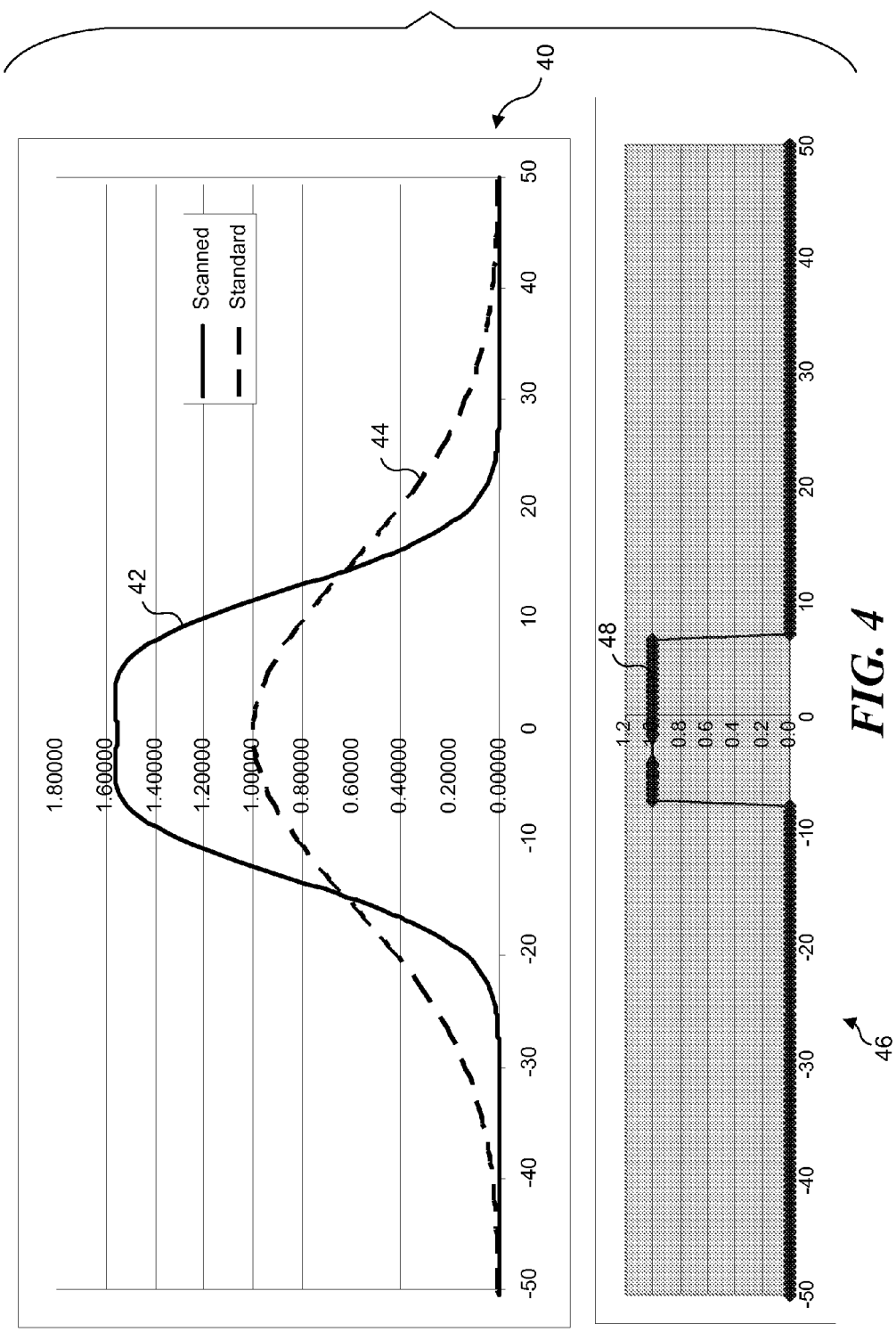
FIG. 4 is similar to FIG. 2, but graphically illustrates the changes when a laser beam with a 30 micron waist is scanned at an amplitude of 12 microns.

FIG. 4 is similar to FIGS. 2A and 2B, respectively, but graph 40 illustrates the changes when a laser beam with a 30 micron waist at a point where the laser beam may be incident on a particle, is scanned at a scan amplitude of 12 microns at that point. The effective flat topped peak laser beam that is achieved is 140% wider (a solid line 42) than a non-scanned laser beam having the 85 micron waist (a dash line 44), while the intensity of the scanned beam is 157% greater than that obtained using a non-scanned laser beam having the 85 micron waist. Graph 46 illustrates a flat topped peak 48 in FIG. 4. Such a modification would be useful if a wider beam is desired to reduce cell-to-cell exposure variation for critical measurements, and the trade off of a more modest increase in the intensity can be accepted.

Figure 5:
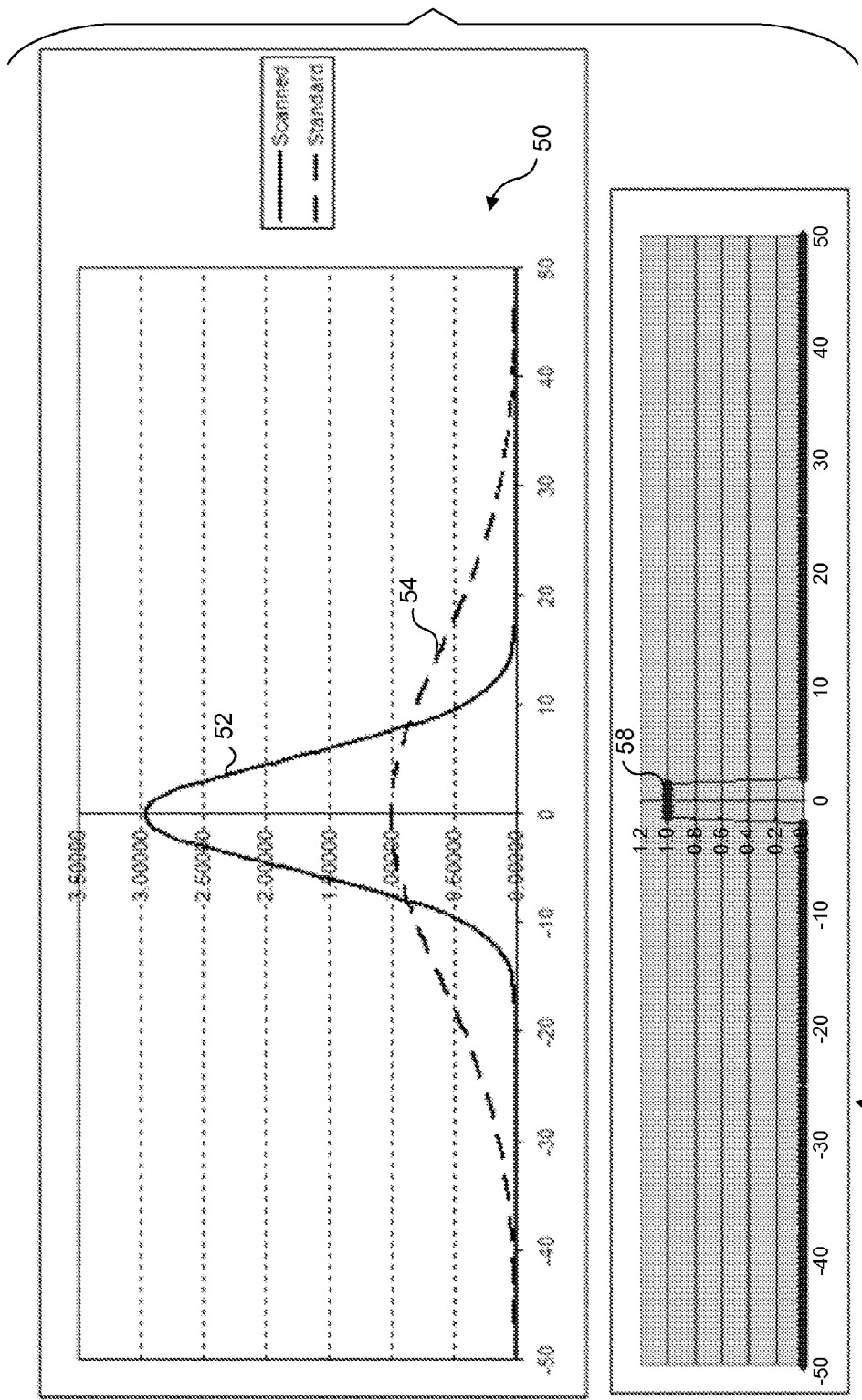
FIG. 5 is similar to FIG. 2, but graphically illustrates the changes when a laser beam with a 15 micron waist is scanned at an amplitude of 6 microns.

Graphs 50 and 56 in FIG. 5 are similar to FIGS. 2A and 2B, respectively, but graph 50 illustrates the changes when a laser beam with a 15 micron waist is scanned at an amplitude of 6 microns. (Again, the waist of the laser beam and the scan amplitude are measured at the point where the laser beam might be incident on a particle in the flow stream or other designated region of a particle analyzer.) The effective beam achieved is 30% narrower (as indicated by a solid line 52) than a non-scanned laser beam having the 85 micron waist (as indicated by a dash line 54), while the intensity of the scanned beam is 314% greater than that obtained using the non-scanned laser beam having the 85 micron waist. Graph 56 indicates a flat topped peak 58 for the scanned laser beam. Such a modification would be useful if a larger cell-to-cell exposure variation is desired, in return for a relatively large increase in the intensity.

Figure 6:
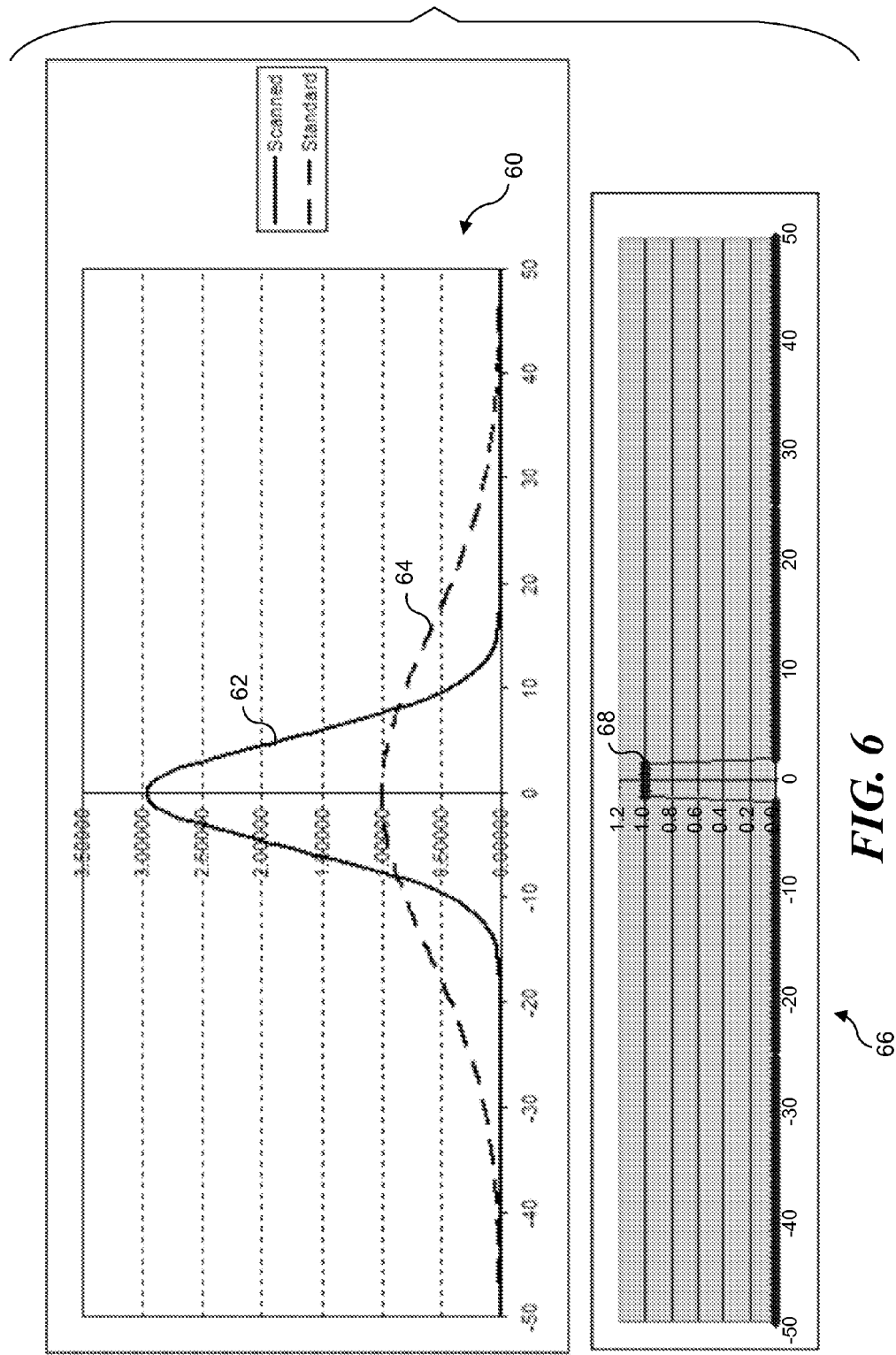
FIG. 6 is similar to FIG. 2, but graphically illustrates the changes when a laser beam with a 25 micron waist is scanned at an amplitude of 4.5 microns.

Graphs 60 and 66 in FIG. 6 are similar to graphs 30 and 36, respectively, in FIG. 2A and FIG. 2B, but graph 60 illustrates the changes when a laser beam with the same 25 micron waist is scanned at an amplitude of 4.5 microns (a solid line 62). In this case, the intensity is three times that of the conventional 85 micron Gaussian beam (a dash line 64), but the uniform region has also decreased by about a factor of three. Changing the scan amplitude is very easy to do in situ to tailor the laser beam profile for a specific application. In this case, the user is willing to sacrifice measurement consistency in order to increase sensitivity. Graph 66 in FIG. 6 illustrates a flat topped profile peak 68 for the scanned laser beam.

A graph 70 in FIG. 7 shows the results for an alternative embodiment of the invention, where the laser beam has a Gaussian profile with an 8 micron waist in the scan axis. The motion profile in this case has been changed to linear with an 8 micron amplitude. In this exemplary embodiment, the intensity (a solid line 72) is more than three fold that of the standard 85 micron Gaussian shown as a dashed line 74, while maintaining the same range of uniformity. It will be understood by those skilled in the art that generation of a something close to a linear profile may be accomplished with a piezoelectric transducer (PZT) and a mirror. However, generation of such a profile takes a significant amount of energy to reverse motion at the ends of the scan. Those skilled in the art will also appreciate that a linear profile may also be generated with an acousto-optic modulator (AOM) or other deflecting devices. However, use of such a device is costly and may lead to energy loss due to loss of the various diffracted orders. Nonetheless, tailoring of the beam size and motion profile may lead to intensity profiles that are advantageous for some applications.

Beam tailoring can be accomplished by changing the amplitude of the beam scanning motion, as well as the specific waveform with which the beam traverses the interrogation region of the instrument. Likewise, the profile may also be affected by the waveform or dimension of the non-scanned beam. In general, the smaller the non-scanned beam diameter before the beam is reflected to scan it, the greater will be the gain in intensity over the conventional Gaussian intensity profile. These Figures demonstrate both sinusoidal beam motion profiles that may be applicable to a resonant scanner, as well as linear profiles suitable for non-resonant scanners. The profile may alternatively also be a ramp, a saw tooth, or a modified sine wave. The frequency of traversal may also be changed, but it is desirable to maintain a sufficiently high scan frequency such that at least one pass is made over the flow cell or region where the beam may be incident on a particle during the time in which a particle traverses the cross section of the beam in the direction orthogonal to the scanning movement of the laser beam. In general, a higher number of passes of the laser beam over the particle is desirable to maintain a more consistent photon dose per particle, as individual particles traverse the illuminated region of the particle analyzer.

As noted above, there are a number of different methods to induce a scanning motion in the beam, to deflect the laser beam over a relatively small amplitude (i.e., an amplitude less than the size of the largest cross-sectional dimension of the laser beam—at the point where the beam might be incident on a particle). One low cost approach is to employ a PZT in conjunction with a mirror on a flexure stage. The piezoelectric crystal of the PZT changes its length in a linear fashion as a function of the voltage applied across the crystal. When affixed to a flexure stage as shown in FIGS. 8A-8D, a change in the length of the PZT causes a shift in the angular attitude of the mirror, thereby deflecting the laser beam through a corresponding arc. If the voltage applied to the crystal changes in a sinusoidal fashion with time, the corresponding angular change in the mirror position will vary accordingly and produce a sinusoidal sweep of the laser beam. Likewise, if the change in the voltage is linear with time, the change in angular attitude will be linear, causing a linear time variant sweep of the beam. In all cases, for the purposes of this novel approach, the amplitude of the sweep or scan of the laser beam is less than the diameter or cross-sectional dimension of the laser beam, where both the size of the laser beam and the amplitude are measured at the point where the laser beam might be incident on a particle.

Those skilled in the art will appreciate that a PZT can be used in resonant as well as non-resonant scanners. If the sweep frequency of the PZT is several times higher than the resonance frequency of the structure, the mirror may move with diminished amplitude and there may be a phase lag in the movement with respect to the voltage profile applied to the PZT. At frequencies well below the resonant frequency, the movement of the mirror should follow from the motion of the PZT. As the scanned frequency approaches the resonant frequency of the scanning structure, there will be an amplification in the displacement of the mirror when compared to the same amount of energy applied to the structure at a frequencies well above or below the resonance frequency, which illustrates the major benefit of the resonant scanning structure, i.e., very little energy is required to drive the mirror to effect the desired beam deflection if the structure is driven at its resonant frequency. In an exemplary resonant scanning embodiment of the present novel approach, cost is further reduced due to the simplification of the drive circuitry by eliminating the high currents and current reversals required to drive the structure.

FIGS. 8A-8D thus illustrate different views of an exemplary embodiment of a system in accord with the present novel approach, where mirror 14 is driven by a first PZT (PZT1) 90, with a second PZT (PZT2) 92 used as a means to preload the first PZT, and also as a means to monitor the amplitude of movement of the first PZT. Flexure stages 16 supporting the mirror are approximately 4 mm by 4 mm in cross section and 3 mm long. They support glass mirror 14, which is sized to be about 25 mm wide by 15 mm tall by 3 mm thick. PZT1 is used to drive the structure, while PZT2 is used as a preload and monitoring device and is adjustable with a preload screw 94. Considering the mass and stiffness of all elements in the structure, the resonance frequency was computed to be approximately 20 KHz. Empirical measurement of the resonant frequency confirmed the computed value.

In resonant structures, changes in temperature may induce changes in the modulus of elasticity of the materials used in the structure. Likewise changes in temperature may also induce changes in the size of the structure. Any changes in the modulus or size can affect preloading and ultimately the stiffness of the structure which in turn can change the resonance frequency of the structure. Very small shifts in the resonance frequency of the structure may have a large impact on the motion of the structure for a given amount of energy input into the structure. This in turn may substantially reduce the amplitude of the scanned beam. Therefore, it may be advantageous to monitor the amplitude of motion of the driving member of the structure to ensure it is moving the prescribed amount. In the exemplary embodiment shown in FIGS. 8A-8D, the signal from PZT2 is fed into a proportional-integral-derivative (PID) controller. The PID controller monitors any difference between a desired scan amplitude and the actual scan amplitude as measured by PZT2. The PID controller then actively changes the amplitude of the voltage supplied to PZT1 in order to minimize any difference between the desired and actual amplitude of the scan motion. Those skilled in the art will appreciate there are many other options for deflecting the beam and controlling the amplitude of the deflection, which when employed, will not depart from the spirit and intent of the present novel approach.

FIG. 9 is a schematic illustration 100 of a scanned and focused laser beam 102 incident on a particle 104 in a core stream 24 of a particle analyzer (not fully shown). This Figure illustrates how the exemplary scanned and focus laser beam having a waist of about 25 microns is scanned with an amplitude of about 9.6 microns, which is substantially less than the waist or diameter of the laser beam where it is incident on particle 104. Scanned and focused laser beam 102 completes at least one scan cycle as the particle is illuminated by the laser beam, and subsequent particles passing through the interrogation region of core stream 24 are then similarly scanned. The illumination of the particles by the laser beam can be used for analyzing the particles, e.g., based on a fluorescence emitted from the particles in response to their illumination by the laser light, but it will be understood that many other forms of analysis and imaging of the particles can be implemented in such a particle analyzer.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. Apparatus for generating an effective flat top intensity profile for light illuminating moving particles in a particle analyzer, comprising:
   (a) a source of light;
   (b) at least one optical component for focusing the light from the source as a beam that is incident on a particle moving through the particle analyzer; and
   (c) a scanner for scanning the light across the particle at a scan frequency selected so that the particle is illuminated with at least one cycle of the light being scanned, and with an amplitude for the scanning that is selected to be less than a diameter of the beam where it is incident on the particle and so that the light remains incident on the particle as the particle passes through a portion of the particle analyzer, wherein the scan frequency, the amplitude for the scanning, and an intensity profile of the source of light cooperate to generate an effective flat top intensity profile for the light being scanned.

2. The apparatus of claim 1, wherein the source of light comprises a laser.

3. The apparatus of claim 1, wherein the scanner comprises an item selected from the group consisting of:
   (a) an acousto-optical modulator;
   (b) an acousto-optical deflector;
   (c) a reflective device that is moved periodically; and
   (d) a diffractive device.

4. The apparatus of claim 1, wherein the scanner includes a reflective surface and an actuator for moving the reflective surface to scan the light reflected from the reflective surface.

5. The apparatus of claim 4, wherein the reflective surface comprises a mirror that is supported by at least one flexure that enables the mirror to be deflected in a periodic motion, when driven by the actuator.

6. The apparatus of claim 4, wherein the actuator comprises at least one piezoelectric transducer.

7. The apparatus of claim 1, wherein the scanner is driven to deflect the light being scanned at about a resonant frequency of the scanner.

8. The apparatus of claim 1, wherein the at least one optical component comprises one or more lenses that focus a beam of the light from the scanner onto the particle in the particle analyzer, reducing a diameter of beam and increasing an intensity of the light incident on the particle.

9. The apparatus of claim 1, wherein a rate at which the scanner scans the light changes as a function of a frequency of a drive signal that is applied to the scanner to drive it.

10. The apparatus of claim 1, wherein a motion profile of the scanned beam varies in according with at least one motion profile selected from the group consisting of:
    (a) sinusoidal motion profile;
    (b) a linear motion profile;
    (c) a saw tooth motion profile; and
    (d) a modified sinusoidal motion profile.

11. The apparatus of claim 1, wherein the scanner includes a reflective surface that is driven to move so that the amplitude of the scanning where the beam is incident on the particle is in the range from about 4.5 microns to about 12.0 microns.

12. The apparatus of claim 1, wherein the scanner directs the beam of the light that is scanned onto a portion of the particle analyzer through which a plurality of particles pass in succession, so that the plurality of particles are scanned by the beam.

13. A method for generating a flat top intensity profile for light illuminating moving particles in a particle analyzer, comprising the steps of:
    (a) directing light from a source toward a scanner;
    (b) scanning the light from the source that is incident on the scanner, to produce scanned light, the scanner being driven to scan a beam of the light at a desired frequency and with a desired amplitude; and (c) focusing the scanned light onto a portion of the particle analyzer through which a particle is disposed, such that a particle in the portion of the particle analyzer is illuminated, wherein the desired frequency is selected so that the particle is illuminated with at least one cycle of the scanned light, and the desired amplitude for the scanning is selected to be less than a cross-sectional dimension of the beam, both the desired amplitude and the cross-sectional dimension of the beam being measured at a point where the beam is incident on the particle, and so that the beam remains incident on the particle as the particle is scanned by the beam within the portion of the particle analyzer, the desired frequency, the desired amplitude for the scanning, and an intensity profile of the source of the light cooperating to generate a flat top intensity profile for the scanned light that is focused on the particle.

14. The method of claim 13, further comprising the step of producing the light using a laser source.

15. The method of claim 13, wherein the step of scanning comprises the step of deflecting the beam using either an acousto-optical modulator, an acousto-optical deflector, a moving reflective surface, or a diffractive device.

16. The method of claim 13, wherein the step of scanning comprises the step of scanning the light from a reflective surface that is moved by an actuator in accord with a desired motion profile.

17. The method of claim 16, wherein the step of scanning comprises the step of supporting a mirror comprising the reflective surface using at least one flexure that enables the mirror to be deflected when moved by the actuator.

18. The method of claim 16, wherein the step of scanning comprises the step of applying a drive signal to an actuator comprising at least one piezoelectric transducer.

19. The method of claim 13, wherein the step of scanning comprises the step of scanning the light at about a resonant frequency of the scanner.

20. The method of claim 13, wherein the step of focusing the scanned light comprises the step of positioning at least one optical component between the scanner and the portion of the particle analyzer through which the particle is passing, the at least one optical component comprising one or more lenses that focus a beam of the light from the scanner onto the particle as the particle is passing through the particle analyzer, reducing a diameter of the beam and increasing an intensity of the light that is incident on the particle.

21. The method of claim 13, wherein the step of scanning comprises the step of changing a rate at which the scanner scans the light as a function of a drive signal that is applied to the scanner to drive it.

22. The method of claim 13, wherein the step of scanning comprises the step of driving the scanner to scan the light with at least one motion profile selected from the group consisting of:

(a) sinusoidal motion profile;

(b) a linear motion profile;

(c) a saw tooth motion profile; and (d) a modified sinusoidal motion profile.

23. The method of claim 13, wherein the step of scanning comprises the step of driving a reflective surface that reflects the light to move with an amplitude that is in the range from about 4.5 microns to about 12.0 microns.

24. The method of claim 13, wherein the step of scanning comprises the step of directing the scanned light onto a portion of the particle analyzer through which a plurality of particles are moving.

25. Apparatus for producing light having an effective flat top intensity profile for illuminating a sample disposed within a particle analyzer, comprising:

(a) a source of light;

(b) a deflecting component that is mounted to receive incident light from the source and to deflect the incident light in a periodic manner, to produce a beam of scanned light that is directed toward a sample volume of the particle analyzer, the deflecting component being driven to scan the beam at a frequency selected so as to illuminate a sample in the sample volume of the particle analyzer with at least one cycle of the scanned light and with an amplitude selected to be less than a cross-sectional dimension of the beam of the scanned light as measured at a point where the beam is incident on the sample and so that the sample is fully illuminated with the scanned light while the sample is in the sample volume of the particle analyzer; and (c) one or more lenses that focus the scanned light onto a sample in the sample volume of the particle analyzer, a peak of an intensity profile of the light produced by the source being of a lower magnitude than a peak of the effective flat topped intensity profile of the scanned light that illuminates the sample volume, due to an increased intensity of the scanned light caused by focusing the scanned light with the one or more lenses and the flat topped intensity profile of the scanned and focused light being caused by scanning the light with the deflecting component at the frequency and amplitude.

* * * * *